United States Patent [19]

Bercu et al.

[11] Patent Number: 5,811,074
[45] Date of Patent: Sep. 22, 1998

[54] METHOD OF DIAGNOSING PITUITARY DEPENDENT GROWTH HORMONE DEFICIENCY

[75] Inventors: Barry B. Bercu, Tampa; Richard F. Walker, Indian Rocks Beach, both of Fla.

[73] Assignee: University of South Florida, Tampa, Fla.

[21] Appl. No.: 722,294

[22] Filed: Sep. 30, 1996

Related U.S. Application Data

[63] Continuation-in-part of Ser. No. 405,842, Mar. 17, 1995, abandoned, which is a continuation-in-part of Ser. No. 171,346, Dec. 21, 1993, abandoned, which is a continuation of Ser. No. 905,760, Jun. 29, 1992, abandoned.

[51] Int. Cl.[6] .......................... G01N 33/50; A61K 38/04; A61K 38/25
[52] U.S. Cl. ........................... 424/9.1; 424/9.2; 424/562; 424/565; 435/7.1; 436/518; 436/86; 514/12; 514/16; 514/17; 600/301
[58] Field of Search ................... 435/7.1, 975; 436/518, 436/86, 811; 424/9.1, 9.2, 562, 565; 514/16, 17, 12; 128/630; 600/301

[56] References Cited

U.S. PATENT DOCUMENTS

| | | |
|---|---|---|
| Re. 33,699 | 9/1991 | Drengler ................................. 424/422 |
| 4,517,181 | 5/1985 | Ling et al. ............................... 514/12 |
| 4,518,586 | 5/1985 | Rivier et al. ............................ 514/12 |
| 4,528,190 | 7/1985 | Vale, Jr. et al. ......................... 514/12 |
| 4,529,595 | 7/1985 | Rivier et al. ............................ 514/12 |
| 4,562,175 | 12/1985 | Chang et al. ........................... 514/12 |
| 4,563,352 | 1/1986 | Rivier et al. ............................ 514/12 |
| 4,585,756 | 4/1986 | Brazeau, Jr. et al. ................... 514/12 |
| 4,595,676 | 6/1986 | Spiess et al. ............................ 514/12 |
| 4,605,643 | 8/1986 | Bohlen et al. .......................... 514/12 |
| 4,610,976 | 9/1986 | Bohlen et al. .......................... 514/12 |
| 4,617,149 | 10/1986 | DiMarchi et al. ..................... 530/324 |
| 4,622,312 | 11/1986 | Felix et al. .............................. 514/12 |
| 4,626,523 | 12/1986 | Vale, Jr. et al. ......................... 514/12 |
| 4,649,131 | 3/1987 | Felix et al. .............................. 514/12 |
| 4,662,312 | 5/1987 | Aoki ....................................... 118/688 |
| 4,710,382 | 12/1987 | Recker ................................... 424/108 |
| 4,774,319 | 9/1988 | Ono et al. .............................. 530/324 |
| 4,844,096 | 7/1989 | Bercu ..................................... 128/630 |
| 5,065,747 | 11/1991 | Bercu ..................................... 128/630 |
| 5,246,920 | 9/1993 | Bercu et al. ............................ 514/12 |

FOREIGN PATENT DOCUMENTS

94/00759  1/1994  WIPO .

OTHER PUBLICATIONS

Cordido et al., 1993. Massive growth hormone (GH) discharge in obese subjects after the combined administration of GH–releasing hormone and GHRP–6: evidence for a marked somatotroph secretory capability in obesity. J. Clin. Endocrinol. Metab. 76: 819–823.

Gertz et al., 1993. Growth hormone response in man to L–692,429, a novel nonpeptide mimic growth hormone–releasing peptide–6. J. Clin. Endocrinol. Metab. 77: 1393–1397.

Albini et al., "Diagnostic value of the growth hormone–releasing factor stimulation test" *Clinical Pharmacol Ther.*, 43:696–700 (1988).

Abribat et al., "Characterization of [I–Try] human growth hormone–releasing factor (1–44) amide binding to rat pituitary . . . " *Brain. Res.*, 528:291–299 (1990).

Abribat et al., "Alterations of pituitary growth hormone–releasing factor binding sites in aging rats" *Endocrinology*, 128:633–635 (1991).

Bercu et al., "Role of selected endogenous peptides in growth hormone releasing hexapeptide (GHRP–6) activity" *Endocrinology*, 130:2579–2586 (1992a).

Bercu et al., "Structural and functional responses of aged female rats to chronic co–administration of growth . . . " *Abstract*, Annual Mtg., San Antonio, TX, Jun. 1992, p. 182 (1992b).

Blake and Smith, "Desensitization studies using perifused rat pituitary cells show growth hormone . . . " *Endocrinol.*, 129:11–19 (1991).

Bowers et al., "Structure–activity relationships of synthetic pentapeptide that specifically . . . " *Endocrinol.*, 106:663–667 (1980).

Bowers et al., "Growth hormone (GH)–releasing peptide stimulates GH release in normal men and acts . . . " *Endocrinol. Metab.*, 70:975–982 (1990).

Bowers et al., "Growth hormone (GH)–releasing activity of a synthetic hexapeptide in normal men and short statured children . . . " *Endocrinol. Metab.*, 74:292–298 (1991).

Butenandt, "Diagnostic value of growth hormone–releasing hormone in short children" *Acta Paediatr. Scand (Supp.)*, 349:93–99 (1989).

Ceda et al., "Diminished pituitary responsiveness to growth hormone–releasing factor in aging male rats" *Endocrin.*, 118:2109–2114 (1986).

Chatelain et al., "Growth hormone (GH) response to single intravenous injection of synthetic GH–releasing . . . " *J. Clin. Endorinol. Metab.*, 65:387–394 (1987).

Cheng et al., "Synergistic effects of HIS–D–TRP–ALA–TRP–D–PHE–LYS–NH" *Endocrinol*, 124:2971–2798 (1989).

(List continued on next page.)

*Primary Examiner*—Paula K. Hutzell
*Assistant Examiner*—James L. Grun
*Attorney, Agent, or Firm*—Kohn & Associates

[57] ABSTRACT

A diagnostic protocol and kit for evaluating pituitary growth hormone (GH) secretory capability as a means to identify the etiology of GH deficiency in children and adults is disclosed. The inventive protocol includes measuring GH secretion, provoked by independent, sequential administration of the xenobiotic GH releasing hexapeptide (GHRP-6) or any of its peptidyl or non-peptidyl synthetic analogues (GHRX) that release GH by the same cellular mechanism as GHRP-6 followed by the naturally occurring GH releasing hormone or its analogues (GHRH) to children and adults afflicted with disorders related to GH deficiency. After evaluating the effects of independent, sequential administration of the GH secretagogues upon changes in blood GH concentrations, the effect of the co-administered GH secretagogues on blood GH concentrations in the child or adult subject is then measured.

8 Claims, 5 Drawing Sheets

OTHER PUBLICATIONS

Codd et al., "Binding of growth hormone releasing hexapeptide to specific hypothalamic and pituitary binding sites" *Neuropharmacology*, 28:1139–1144 (1989).

DeBell et al., "Growth hormone (GH) secretion during continuous infusion of GH–releasing peptide . . ." *J. Clin. Endocrinol. Metab.*, 72:1312–1316 (1991).

DeGennaro Colonna et al., "Reduced growth hormone releasing factor (GHRF)–like immunoreactivity . . ." *Peptides*, 10:705–708 (1989).

Devesa et al., "Reasons for the variability in growth hormone (GH) responses to GHRH challenges . . ." *Clinical Endocrinology*, 30:367–377 (1989).

Dorland's Illustrated Medical Dictionary, Twenty–fifth Edition, ed. W.B. Saunders, p. 78. "analogue".

Finkelstein et al., "Age–related change in 24–hour spontaneous secretion of growth hormone" *J. Clin. Endocrinol. Metab.*, 35:665–670 (1972).

Ge et al., "Relationship between growth hormone–releasing hormone and somatostatin in rat . . ." *J. Endocrinol.*, 123:53–58 (1989.

Ghigo et al., "Pyridostigmine partially restores GH responsiveness to GHRH in normal aging" *Acta Endocrinol.*, 123:169–174 (1990).

Goth et al., "Pituitary adenylate cyclase activiating polypeptide, growth hormone (GH)–releasing peptide and GH–releasing . . ." *Endrinology*, 130:939–944 (1992).

Ho et al., "Effects of sex and age on 24–hour profile of growth hormone secretion in man . . ." *J. Clin. Endocrinol. Metab.*, 64:51–57 (1987).

Iovino et al., "Repetitive growth hormone–releasing hormone administration restores the attenuated growth hormone . . ." *J. Clin. Endocrinol. Metab.*, 69:910–913 (1989).

Jansson et al., "The dwarf little (Lit/Lit) mouse is resistant to growth hormone releasing peptide . . . " Endocrine Society Abstracts, Annual Meeting, (1986).

Kaiser et al., "Effects of recombinant human growth hormone on malnourished older individuals" *J. Am. Geriatr. Soc.*, 39:235–240 (1991).

Lang et al., "Effects on sex and age on growth hormone response to growth hormone–releasing hormone in healthy individuals" *J. Clin. Endocrinol. Metab.*, 65:535–540 (1987).

Lang et al., "The influence of age on human pacreatic growth hormone releasing hormone stimulated growth . . ." *Horm. Metabol. Res.*, 20:574–578 (1988).

Marcus et al., "Effects of short term administration of recombinant human growth hormone to elderly people" *J. Clin. Endocrinol. Metab.*, 70:519–527 (1990).

Morimoto et al., "Age–related changes in growth hormone releasing factor and somatostatin in rat hypthalamus" *Neuroendocrinology*, 47:459–464 (1988).

Martha et al., "A persistent pattern of varying pituitary responsivity to exogenous growth hormone . . ." *J. Clin. Endocrinol. Metab.*, 67:449–454 (1988).

Merica et al., "Growth hormone responses to a second generation growth hormone releasing peptide . . . " *Endocrine Society Abstracts*, 74th Annual Mtg., San Antonio, TX, No. 477, p. 171, (1992).

Momany et al., "Design, synthesis, and biological activity of peptides which release growth hormone in vitro" *Endocrinol.*, 108/31–39 (1981).

Momany et al., "Conformational energy studies and in vitro and in vivo activity data on growth hormone–releasing peptides" *Endocrinol.*, 114:1531–1535 (1984).

Ono et al., "Release of immunoreactive growth hormone–releasing factor (GRF) and somatostatin from incubated . . . " *Neuroendocrinology*, 43:111 (Abstract) (1986).

Parenti et al., "Different regulation of growth hormone–releasing factor–sensitive adenylate cyclase in anterior pituitary . . . " *Endocrinology*, 121:1649–1653 (1987).

Pavlov et al., "Responses of growth hormone (GH) and somatomedin–C to GH–releasing hormone . . . " *J. Clin. Endocrinol. Metab.*, 62:595–600 (1986).

Pertzelan et al., "Plasma growth hormone response to synthetic GH–RH1–44 in 52 children . . . " *Hormone Res.*, 22:24–31 (1985).

Robinson et al., "Acute growth hormone (GH) response to GH–releasing hexapeptide in humans in independent . . . " *J. Clin. Endocrinol. Metab.* 75:1121–1124 (1992).

Root and Oski, "Effects of human growth hormone in elderly males" *J. Gerontol.*, 24:97–104 (1969).

Rudman et al., "Impaired growth hormone secretion in adult population" *J. Clin. Invest.*, 67:1361–1369 (1981).

Rudman et al., "Effects of human growth hormone in men over 60 years old" *New Eng. J. Med.*, 323:1–6 (1990).

Schriock et al., "Effect of growth hormone (GH)–releasing hormone (GRH) on plasma GH in relation . . . " *J. Clin. Endocrinol. Metab.*, 58:1043–4049 (1984).

Shibasaki et al., "Age–related changes in plasma growth hormone response to growth hormone–releasing factor in man" *J. Clin. Endocrinol. Metab.*, 58:212–214 (1984).

Smith et al., "A nonpeptidyl growth hormone secretagogue" *Science*, 260:1640–1643 (1993).

Sonntag et al., "Decreased pulsatile release of growth hormone in old male rats" *Endocrinology*, 107:1875–1879 (1980).

Sonntag et al., "Effects of CNS active drugs and somatostatin antiserum on growth hormone release . . . "*Neuroendocrinology*, 33:73–78 (1981).

Sonntag et al., "Impaired ability of old male rats to secrete growth hormone in vivo but not in vitro in response . . . " *Endocrinology*, 113:2305–2307 (1983).

Sonntag et al., "Growth hormone releasing hormone induced release of growth hormone in aging male rats . . . " *Neuroendocrinology*, 47:482–488 (1988).

Takahashi et al., "Growth hormone secretory patterns in young, middle–aged and old female rats" *Neuroendocrinology*, 46:137–142 (1987).

Tannenbaum et al., "Paradoxical enhancement of pituitary growth hormone (GH) responsiveness to GH–releasing factor in the face . . . " *Endocrinology*, 124:1380–1388 (1989).

Walker et al., "Robust growth hormone (GH) secretion in aged female rats co–administered GH–releasing . . . " *Life Science*, 49:1499–1504 (1992).

Walker et al., "Effects of stimulated growth hormone secretion on age–related changes in plasma cholesterol . . . " Mechanisms of Aging and Development, 75:215–226 (1994a).

Walker et al., "Effects of growth hormone secretagogues on age–related changes in the rat immune system" *Endocrine*, 2:857–862 (1994b).

Wehrenberg and Ling, "Absence of age–related change in pituitary response to growth hormone–releasing factor . . . " *Neuroendocrinology*, 37:463–466 (1983).

Howard et al., "A receptor in pituitary and hypothalamus that functions in growth hormone release" *Science*, vol. 273, pp. 974–977 (1996).

METHOD OF DIAGNOSING PITUITARY DEPENDENT GROWTH HORMONE DEFICIENCY

This application is a Continuation-In-Part of U.S. Ser. No. 08/405,842, filed Mar. 17, 1995, now abandoned which is a Continuation-In-Part application of U.S. Ser. No. 08/171,346, filed Dec. 21, 1993, now abandoned which was a Continuation application of U.S. Ser. No. 07/905,760, filed Jun. 29, 1992, now abandoned.

BACKGROUND OF THE INVENTION

1. Technical Field

The present invention provides a method for directly testing pituitary GH secretory capability in children and adults with clinical symptoms of growth hormone deficiency.

2. Background Art

Stimulated growth hormone (GH) secretion by a variety of provocative agents including L-dopa, clonidine, arginine and insulin has been used to assess GH secretory capability in children with short stature and in adults with a variety of disorders associated with GH deficiency, such as osteoporosis, muscle atrophy, reduced LDL cholesterol metabolism, poor immune function, etc. However, the reliability of those provocative agents has been the subject of significant debate because differential GH secretion in subsets of patients makes the data difficult to interpret. Significant variability presumably occurs because the GH stimulating mechanisms of these non-specific, provocative agents are not well defined and probably affect various different levels of the GH regulatory cascade, ranging from hypothalamic to pituitary sites.

For example, the non-specific provocative agents whose action may be mediated, at least in part, by release of growth hormone releasing hormone (GHRH) from the brain, cannot differentiate between deficient hypothalamic GHRH stores or release capabilities from unresponsive pituitary-GHRH transduction mechanisms. Thus, the isolation, characterization and synthesis of naturally occurring GHRH and its structurally altered analogues that act directly upon the pituitary by the same mechanism as GHRH, seemed to provide a potentially valuable diagnostic tool for differentiating GH deficiency resulting from hypothalamic versus pituitary deficits (Butenandt, 1989). However, its diagnostic value has been surprisingly limited because of marked and unexpected variability in GH secretion following administration of GHRH, i.e., in some cases GHRH showed extremely low potency even though pituitary GH secretory mechanisms were intact (Pertzelan, 1985).

In an attempt to explain this variability, it was proposed that some children and adults with GH deficiency due to inadequate hypothalamic GHRH release were hyporesponsive to a single dose of GHRH because of chronic deprivation of the exposure to the peptide (Schriock et al., 1984). This explanation was not completely adequate because subnormal GH responses to a single GHRH injection were also observed in GH sufficient children and adults (Chatelain et al., 1987; Pavlov et al., 1986).

Another proposal to explain variable responses to provocative GHRH tests was that GH releasing activity of the peptide varied with the time of its administration (Martha et al., 1988). Endogenous hypothalamic-somatotroph secretory rhythms affect the GH response to GHRH in humans (Devesa et al., 1989), and rats in vivo (Albini et al., 1988) and in vitro (Tannenbaum et al., 1989) and this rhythm might cause the variation in GH responsivity following exogenous GHRH.

Thus, debate has considered whether spontaneous as well as stimulated GH secretion must be characterized to reliably identify children and adults with low GH secretion. Clearly, the greatest information would be derived from both methods, but the high cost and inconvenience of extended hospitalization for long-term analysis of spontaneous GH secretion limits the practical utility of this procedure. On the other hand, the low cost and relatively rapid, provocative procedure makes this type of testing most attractive, so long as the problem of response variability could be resolved.

U.S. Pat. Nos. 5,065,747 issued Nov. 19, 1991, and 4,844,096 issued Jul. 4, 1989 describe methods for reducing the variability in GH response levels by administering somatostatin prior to provocative testing for the purpose of determining the etiology of growth hormone deficiency. Variability in responses still occur with this protocol suggesting that the responses are modulated by other factors.

In addition, there is a reciprocal relationship between endogenous growth hormone (GH) and degenerative changes in form and function associated with aging. For example, the correlation between low serum GH concentrations and somatic involution/physiologic dysfunction was recognized decades ago (Root and Oski, 1969; Rudman et al., 1981). However, limited availability of cadaver-derived GH prior to development of recombinant biotechnological methods prevented valid testing of the hypothesis that GH deficiencies and aging decrements were functionally related. When GH became available for experimentation, it was possible to show that administration of the hormone to old men significantly increased insulin-like growth factor-1 (IGF-1), urinary nitrogen retention, body weight gain, lean body mass, bone density, renal function and improved psychological attitude (Rudman et al., 1990; Kaiser et al., 1991; Marcus et al., 1990). Thus, while patterns of spontaneous GH secretion deteriorate and serum GH concentration decline during aging (Finkelstein et al., 1972; Rudman et al., 1981; Ho et al., 1987), somatic responsiveness to GH seems to remain intact, since insulin-like growth factor-1 (IGF-1; somatomedin-C) decrements and certain physical/physiological deficits are readily reversed by administration of exogenous GH (Pavlov et al., 1986).

There is progressive resistance to GH secretion during aging that results from either inadequate stimulation of the pituitary gland or degeneration of pituitary-based mechanisms for GH production/secretion. Except for two reports (Wehrenberg and Ling, 1983; Pavlov et al., 1986), there is a consensus that GH secretion in response to GHRH administration in vivo declines with advancing age (Ceda et al., 1986; Ghigo et al., 1990; Iovino et al., 1989; Lang et al., 1987, 1988; Shibasaki et al., 1984; Sonntag and Gough, 1988; Sonntag et al., 1980, 1983). It is possible that changes in the relationship of GH regulatory hormones of hypothalamic origin are the primary etiological factors in age-related decline in GH secretion. Since several hormones may be involved, provocative tests with GHRH alone to determine GH secretory capability in older adults with clinical symptoms of GH deficiency may not be adequate.

Applicants have previously attempted to provide a protocol which would determine GH secretory capability, i.e. deficiencies, in adults and children utilizing combined testing with growth hormone releasing hormone (GHRH) and xenobiotic GH releasing hexapeptide (designated GHRP-6 or GHRP) (see U.S. Pat. No. 5,246,920 and WO 94/00759). However, unexpected variability in responses and reproducibility continued utilizing the methods set forth in the above listed references.

It is, therefore, an objective of the present invention to provide a diagnostic protocol that can differentiate between various etiologies of GH deficiency in both children and adults and that is reproducible and with low variability.

SUMMARY OF THE INVENTION AND ADVANTAGES

According to the present invention, a diagnostic protocol and kit for evaluating pituitary growth hormone (GH) secretory capability as a means to identify the etiology of GH deficiency in children and adults is disclosed. The inventive protocol includes measuring GH secretion, as determined by changes in serum, plasma, or whole blood GH concentrations following provocative challenge to children and adults afflicted with disorders related to GH deficiency. The challenge comprises administration first of the xenobiotic GH releasing hexapeptide (GHRP-6) or any of its peptidyl or non-peptidyl synthetic analogues that release GH by the same cellular mechanism as GHRP-6 (the group/family of compounds are referred to as GHRX). Within two to four hours of the GHRX administration the naturally occurring GH releasing hormone (GHRH) or its peptidyl or non-peptidyl synthetic analogues that release GH by the same cellular mechanism as GHRH (the group/family of compounds are referred to as GHRH) is then administered. GH secretion is measured at regular intervals for two hours after administration of each GH secretagogue. After evaluating the effects of independent, sequential administration, the effect of co-administration of the GH secretagogues on blood GH levels is determined on a different day.

In the preferred embodiment, the changes in serum, plasma or whole blood concentrations of GH following individual administration of these two different GH secretagogues is then expressed as a ratio of peak GH concentrations for GHRX divided by peak GH concentrations for GHRH.

This ratio is then used to compare the results for the subject being tested against values derived from normal subjects for reference purposes. The ratio provides a relative measure of the deficiency for each endogenous secretagogue in reference to the co-secretagogue. This is useful in selecting the therapeutic dose for treatment since the more the ratio deviates from the normal range the more aggressive the treatment must be.

The present invention provides a new and more effective way to use stimulated GH secretion as a reliable and effective tool for directly evaluating pituitary GH secretory capability and for differentiating specific extra-pituitary factors from intra-pituitary factors that contribute to GH deficiency in children and adults afflicted with medical disorders related to such a hormone deficit. In particular the present invention removes the variability and lack of reproducibility of the prior art methods.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

The present invention provides a diagnostic procedure and kit for determining whether growth hormone (GH) deficiency in children and adults is due to a deficiency in endogenous growth hormone releasing hormone (GHRH), to a deficiency of the endogenous analogue of a new family of xenobiotic GH secretagogues (GHRX), the prototype of which is GHRP-6, to a deficiency of both endogenous GH secretagogues, or due to intrinsic defects in the pituitary gland not involving either GH secretagogue, that result in GH deficiency.

GHRH has been identified as a naturally occurring GH secretagogue. GHRP-6 represents a synthetic analogue of another, yet unidentified, endogenous GH secretagogue. Although the endogenous substance remains unidentified its receptor has been defined (Howard et al., 1996). The relationship between GHRP-6 and its endogenous counterpart is presumably analogous to that of morphine and the endorphins.

Since GHRH and GHRP-6 are functional complements, the response of one is amplified in the presence or under the influence of the other. Therefore, robust GH secretion in response to administration of GHRH or GHRP-6 could be interpreted as representing adequate endogenous GHRP-6 or GHRH, respectively. Alternatively, assuming that all pituitary cellular and molecular elements for GHRH- and GHRP-6-mediated GH secretion are functional, a poor response to either GH secretagogue administered individually could represent inadequacy of its endogenous complement. The paradox in this hypothesis is that a normal response to a provocative challenge by a given GH secretagogue will be observed for the peptide that is lacking or deficient in the patient.

Utilizing this differential diagnostic procedure, the integrity of functional pituitary elements can be differentiated from inadequate concentrations of both endogenous complements by administering the GH secretagogues simultaneously. GH secretion in response to co-administered GHRH and GHRP-6 would indicate inadequate endogenous GH secretagogues, whereas lack of GH secretion in response to the co-administered secretagogues would indicate the absence of endogenous GH secretagogues or intrinsic defect (s) in pituitary functional capacity.

The basis of the diagnostic test is a comparison of responses to provocative challenges of exogenous/endogenous GH secretagogues administered sequentially and in combination. However, as shown herein below Applicants have determined unexpectedly that the order of the testing and timing of the injections of the two components is critical to accurate, reproducible results.

GHRH and GHRP-6 or their peptidyl or non-peptidyl synthetic analogues that release GH by the same cellular mechanism as GHRH and GHRP-6 respectively are used as the GH secretagogues. For clarity of discussion, the invention will be discussed mainly in terms of GHRH and GHRP-6. The invention, however, may be applied in a homologous fashion with the analogues of these two GH secretagogues.

The analogues for xenobiotic GHRP-6 include peptidyl and non-peptidyl forms of GHRP-6-like xenobiotic GH secretagogues that release growth hormone from the pituitary gland by the same cellular mechanism as GHRP-6. The group/family of these related molecules are designated as GHRX. The analogues of GHRH are members of a group of GH secretagogues which can be referred to growth hormone releasing compound (GHRC) such as GH releasing hormone (GHRH), GH releasing factor or any of its synthetic analogues that release GH from the pituitary gland by the same cellular and molecular mechanism as GHRH. However, by convention this group/family of related molecules is referred to as GHRH.

The diagnostic procedure of the present invention is carried out by establishing baseline levels of growth hormone (GH) in the blood of the child or adult being evaluated. Sequential, independent provocative challenges are administered in the order GHRX followed by GHRH, and then the combination of the GH secretagogues is administered.

The timing between the sequential, independent challenges must be between two and four hours with the preferred embodiment at two hours (120 minutes after GHRX administration). Blood is drawn at regular intervals for up to two hours after the administration of each secretagogue, generally every 5 minutes for the first 20 minutes after administration and 10–15 minute intervals thereafter for the remaining two hours. From these blood samples the peak GH response is measured thereby determining if GH level changes after each administration has occurred.

On a separate day from the sequential administration of the two GH secretagogues, a combination of GHRH and GHRX is administered as a single intravenous bolus. Blood samples are drawn at the same time intervals as following administration of the sequential individual challenges for up to three hours after administration of the combination.

The diagnostic potential of GHRX and GHRH, with GHRP and growth hormone releasing hormone respectively the preferred compounds, for determining the etiology of GH secretory deficiency is profoundly affected by the sequence in which the secretagogues are administered. When GHRH is administered alone, the GH secretory response it elicits is extremely variable and is poorly dose related (Table 1).

TABLE 1

| GHRH ($\mu$g/kg) | Peak Serum GH (ng/ml) $\bar{x} \pm$ SEM |
|---|---|
| 0 | 1.09 ± 1.02 |
| 0.1 | 9.46 ± 3.71 |
| 0.33 | 16.45 ± 8.11 |
| 1.0 | 13.54 ± 6.51 |
| 3.3 | 21.80 ± 6.78 |
| 10.0 | 17.41 ± 4.67 |

Current knowledge of GHRH stimulated GH secretion attributes the variability of GHRH to the physiological state of the GH neuroendocrine axis at the time that the stimulus is applied (Devesa et al., 1989; Albini et al., 1988; Tannenbaum et al., 1989). In other words, the sensitivity or readiness of the GH neurosecretory system to stimulation is dynamic, sometimes being greater than other times. Since the physiological factors affecting sensitivity to GHRH stimulation are not easily predicted immediately prior to a GHRH challenge, it is essentially impossible to eliminate variability if GHRH is administered by itself or before GHRP.

On the other hand, the response to GHRP administered alone is not variable (Table 2). The minimal variability of the GHRP response is presumed to result from its partial action as a somatostatin agonist.

TABLE 2

| GHRP ($\mu$g/kg) | Peak Serum GH (ng/ml) $\bar{x} \pm$ SEM |
|---|---|
| 0 | 1.11 ± 1.01 |
| 0.1 | 17.51 ± 1.91 |
| 0.5 | 41.31 ± 3.97 |
| 1.0 | 67.88 ± 6.1 |
| 1.5 | 81.60 ± 5.88 |

Relevant to using GHRH and GHRP as diagnostic agents is the fact that GHRP eliminates the endogenous factors causing variability in the GHRH response. Administration before GHRH creates an episode of GH secretion that "resets" the sensitivity of the GH neurosecretory axis to stimulation by GHRH, so that at the time of GHRH administration, uniform baseline conditions in the subject have been achieved. This then puts the GH neurosecretory axis in a uniform state of readiness for GHRH so that a subsequent relatively stable and constant episode of GHRH-stimulated GH secretion results (Table 3). This GHRH stimulated GH secretory episode can then be compared with the stable episode of GHRP-stimulated GH secretion that preceded it as a basis for the diagnostic test of the present invention. In Table 3 the GH secretory responses in the same individual to repeated injections of GHRH preceded by GHRP shows stable response to GHRP and GHRH. The GHRH variability is significantly reduced.

TABLE 3

| GH Secretagogue ($\mu$g/kg) | Peak Serum GH (ng/ml) $\bar{x} \pm$ SEM |
|---|---|
| GHRP 1.0 | 69.31 ± 4.21 |
| GHRH 1.0 | 32.66 ± 3.33 |

In summary, five conditions are anticipated: normal, an insufficiency of GHRH, an insufficiency of the in vivo endogenous analogue of GHRP-6, an insufficiency of both or a defective pituitary GH secretory mechanism. The last four conditions will present with a GH insufficiency. Obviously, the cause in each case is different. In each of these conditions, a different pattern of GH secretion is anticipated in response to a provocative challenge with exogenous GHRC and GHRX. (Table 4). It is these different responses that are used to differentially diagnose the etiology of GH insufficiency, i.e. to determine whether the GH insufficiency is based upon GHRH and/or in vivo endogenous analogue of GHRP-6 insufficiency, or upon an inherent, functional pituitary defect.

In Table 4 the first column lists the stimulus or provocative challenge given to the patient. Columns 2–5 list the possible status of endogenous GH secretagogues. The predicted response, increase in GH concentration, to the challenge is listed in each column and is dependent upon the endogenous status of the GH secretagogues.

TABLE 4

INCREASED BLOOD CONCENTRATIONS OF GH IN RESPONSE TO PROVOCATIVE CHALLENGE

| Provocative Challenge/ Stimulus | GHRH + GHRP + | GHRH − GHRP + | GHRH + GHRP − | Missing Both | Pituitary Mechanistic Defect |
|---|---|---|---|---|---|
| GHRX | Yes | No | Yes | No | No |
| GHRH | Yes | Yes | No | No | No |
| Both | Yes | Yes | Yes | Yes | No |

In the normal condition, GHRH and the in vivo endogenous analogue of GHRP-6 are present in normal concentrations (Column 2, Table 4). Therefore, the injection of GHRX and then GHRH will release concentrations of GH that are normal and that reflect the presence of endogenous GHRH and endogenous analogue of GHRP.

If endogenous GHRH is insufficient or absent while the in vivo endogenous analogue of GHRP-6 is present in normal amounts (column 3, Table 4), the injection of GHRX will release subnormal amounts of GH, if at all. However, an injection of GHRH following the GHRX will release a single normal quantum of GH.

If the in vivo endogenous analogue of GHRP-6 is insufficient or absent while endogenous GHRH is present in normal amounts (Column 4, Table 4), then the injection of GHRX will release a normal quantum of GH. However, the subsequent injection of GHRH will release subnormal amounts of GH, if at all.

If both endogenous GH secretagogues are insufficient or absent (Column 5, Table 4), then GHRX and the subsequent GHRH administration individually will release subnormal quanta of GH, if at all. If the co-administration of GHRH and GHRX release a normal quanta of GH, then both endogenous secretagogues are absent or insufficient. If no or reduced GH is released (Column 6, Table 4) than an intrinsic defect in the pituitary gland not involving either GH secretagogue has been shown.

The responses are evaluated as representing optimal concentrations of both endogenous GH secretagogues or deficiencies of one or the other endogenous complementary secretagogue and by calculating a ratio of peak GH concentrations for GHRX divided by peak GH concentrations for GHRH. The normal range of ratios is calculated and the response of the patient compared with the normal values. A ratio in the range of 1.4 to 2.9 is considered in the normal range.

Normal values for GH secretion and normal ranges are determined for each population tested by sampling from healthy individuals. In the examples herein the population tested was primarily European, male and contained both children and adults. Normal values may be different for other populations depending on factors such as ethnicity, pre- and post menapausal women. In addition environmental factors may be considered such as time of year in establishing normal ranges.

A deficiency in both endogenous peptides would produce a ratio in the normal range. Therefore, whenever a normal ratio is observed the peak values must be checked to determine if the peak responses are in the normal range. If not, then the patient is deficient in both endogenous GH secretagogues. The normal ratio must be achieved with peak GH values for GHRX stimulation ranging between 40 and 90 ng/ml and for GHRH stimulation ranging between 20 and 45 ng/ml. GH values <40 ng/ml or >90 ng/ml from GHRX stimulation or <20 ng/ml or >45 ng/ml from GHRH stimulation suggest abnormal changes in concentrations of the endogenous analogues for both GHRX and GHRH. Alternatively, the pituitary transduction and GH release mechanisms may be abnormal. Co-administration of the GH secretagogues will identify these patients.

Ratios of 3.0 to 3.9 result from relatively greater response to GHRX than to GHRH. This would be due to a decline or modest deficit in endogenous GHRX. Alternatively, an unusually robust response to GHRX without a concomitant robust response to GHRH (i.e., GHRH response remains "normal") can provide a ratio in this range. This response suggests an unusual increase in endogenous GHRH. By analyzing both the ratio and the underlying individual responses these alternatives can be distinguished and identified.

Ratios less than 1.0 suggest severe deficiency in endogenous GHRH without deficiency of endogenous GHRX. Ratios of 1.1 to 1.4 resulting from relatively greater responses to GHRH than to GHRX indicate a modest deficit in endogenous GHRH or an unusual increase in endogenous GHRX. As discussed herein above these can be distinguished based on an analysis of the peak values used to calculate the ratio.

The ratio provides a relative measure of the deficiency for each endogenous secretagogue in reference to the co-secretagogue. This is useful in selecting the therapeutic dose for treatment since the more the ratio deviates from the normal range the more aggressive the treatment must be.

The growth hormone levels in the blood of the child or adult can be measured by any well known procedures, e.g., using an immunoradiometric assay as described by Bowers et al. (1990) or any other contemporary, scientifically accepted method.

In addition to GHRH itself, any growth hormone releasing compound can be utilized in the diagnostic procedure of the present invention. However, GHRH is the preferred growth hormone releasing compound for use in the claimed invention. The growth hormone releasing compounds which may be used in practicing the present invention are any such compounds known to induce growth hormone (GH) secretion and include growth hormone releasing hormone (GHRH) (1-44) and analogues GHRH (1-40) and GHRH (1-29) thereof. There are numerous growth hormone releasing compounds known in the art, and any of these known compounds will be useful in practicing the present invention. U.S. Pat. No. 4,622,312 provides an excellent description of GHRH and analogue thereof, which can be used in the presently claimed invention. Reissue Pat. No. RE33,699 provides a summary of patents which teach growth hormone releasing compounds. The growth hormone releasing compounds taught in each of the following U.S. patents are suitable for invention. Reissue Pat. No. RE 33,699 provides a summary of patents which teach growth hormone releasing compounds taught in each of the following U.S. patents are suitable for use in the method of the present invention:

| COUNTRY | PATENT NO | COLUMN |
|---|---|---|
| U.S. | RE 33,699 | 1–4 |
| U.S. | 4,517,181 | 2 |
| U.S. | 4,518,586 | 1–4 |
| U.S. | 4,528,190 | 1–2 |
| U.S. | 4,529,595 | 1–4 |
| U.S. | 4,562,175 | 1–2 |

-continued

| COUNTRY | PATENT NO | COLUMN |
|---|---|---|
| U.S. | 4,563,352 | 1–4 |
| U.S. | 4,585,756 | 1–2 |
| U.S. | 4,595,676 | 1–2 |
| U.S. | 4,605,643 | 1–2 |
| U.S. | 4,610,976 | 1–2 |
| U.S. | 4,617,149 | 1–4 |
| U.S. | 4,622,312 | 1–4 |
| U.S. | 4,626,523 | 1–2 |
| U.S. | 4,649,131 | 1–4 |
| U.S. | 4,710,382 | 1–2 |
| U.S. | 4,774,319 | 1 |

The above U.S. patents and, in particular, the portions indicated above by column number, are incorporated herein by reference as teaching growth hormone releasing compounds that are useful in the practice of the presently claimed invention.

The term GHRP-6 and analogues thereof (GHRX) means GHRP-6 and any peptide or nonpeptide compound that releases GH by the same cellular mechanism. The term analogue (*Dorland's Illustrated Medical Dictionary*, 25th Edition, W. B. Saunders, Philadelphia, Pa., p. 78) in the present invention is used to refer to functional and metabolic analogues that are peptides or nonpeptides that cause the release of GH by the same cellular mechanism as GHRP-6, i.e., they are compounds of similar activity. GHRP-6 is the hexapeptide His-D-Trp-Ala-Trp-D-Phe-Lys-$NH_2$ which is believed to act directly on the pituitary to release GH. In addition to GHRP-6, the pentapeptide Tyr-D-Trp-Gly-Phe-Met-$NH_2$ (Cheng et al., 1989) is a useful analogue in the release of GH.

Other compounds considered analogues of GHRP-6 for purposes of the present invention have been reported. For example, C. Y. Bowers et al. (1980) teaches that, in addition to Tyr-D-Trp-Gly-Phe-Met-$NH_2$, compounds Tyr-D-Phe-Gly-Phe-Met-$NH_2$ and Trp-D-Phe-Pro-Phe-Met-COOH as being useful in the release of growth hormone, and GHRP-1 having the formula Ala-His-D-β-Nal-Ala-Trp-D-Phe-Lys-$NH_2$ is also useful in the release of growth hormone. Also, Momany et al. (1981) teaches the following compounds as being useful in the release of growth hormone: Try-Ala-D-Trp-Phe-Met-$NH_2$; Tyr-D-Trp-D-Trp-Phe-Met-$NH_2$; Tyr-D-Trp-D-Trp-Phe-$NH_2$; Tyr-D-Trp-D-Trp-Phe-COOH; and D-Trp-D-Trp-Phe-$NH_2$. Additionally, F. A. Momany et al., (1984) teaches the following compounds as being useful in the release of growth hormone: His-D-Trp-Ala-Trp-D-Phe-$NH_2$; His-D-Trp-Ala-Trp-D-Phe-Lys-$NH_2$; Tyr-D-Trp-Ala-Trp-D-Phe-$NH_2$; His-D-Trp-Ala-Trp-D-Phe-Arg-$NH_2$; and His-D-Trp-Ala-Trp-D-Phe-Lys-COOH. Further, U.S. Pat. Nos. 4,839,344 and 4,880,778 to Bowers et al. disclose many of the above peptides. All of these compounds are useful in the diagnostic procedure of the present invention.

A nonpeptide functional or metabolic analogue of GHRP-6 has been disclosed by Smith et al. (1993) that acts through the same site as GHRP-6. The compound, L-692, 429, is antagonized by the same agents as is GHRP-6 and interacted with GRF. This and related compounds activate the same cellular receptors and second messengers as GHRP-6 in the course of initiating its relevant action (e.g. growth hormone release).

All of these analogues and compounds of similar activity are useful in practicing the present invention as described herein; however, these peptides and nonpeptides should not be considered as being exhaustive of the GHRP-6 analogue-compounds useful in practicing the present invention.

The provocative challenge with GHRH must be administered after blood concentrations of GH return to basal levels, i.e. approximately 120 minutes after administration of GHRX.

The quantities of each agent to be administered is any quantity known to be effective in causing an increase in growth hormone levels., i.e., an amount which will stimulate release of growth hormone, and are adjusted to take into account age, sex and body weight as are known in the medical arts. In general, 1 µg/kg body weight has been found to be effective.

The patients are selected for evaluation by the inventive protocol according to the following criteria. Slow growth in children or disorders in children and adults associated with growth hormone deficiency, with or without low blood concentrations of insulin-like growth factor-1 (IGF-1) and insulin-like growth factor binding protein-3 (IBP-3), such as obesity, osteoporosis, skeletal muscle atrophy, reduced lean body mass, frailty, increased serum LDL cholesterol, reduced immune function, etc., are candidates for the differential diagnostic procedure.

Upon testing with the present inventive protocol, patients deficient in GHRH, as indicated by a poor response to GHRP-6 challenge, would be best treated by GHRH replacement therapy. Children or adults deficient in the endogenous analogue for GHRP-6, as indicated by a poor response to GHRH, would be best treated by GHRP-6 replacement therapy. Children or adults deficient in both GH secretagogues, as indicated by poor responses to sequentially administered GHRP-6 and GHRH but with a robust response to co-administered GHRH and GHRP-6, would be best treated by GHRH and GHRP-6 replacement therapy. Children and adults with intrinsic defects in pituitary cellular and/or molecular mechanisms such as GH secretion involving signal transduction (receptors and second messengers), gene expression (transcription or translation), or hormone release, as indicated by a poor response to all challenges, would not respond to therapy with GH secretagogues. Instead, these patients would best benefit from recombinant GH replacement therapy.

The present invention also provides for a kit for the differential diagnosis of pituitary dependent growth hormone deficiency. The kit includes an amount of one of a growth hormone releasing compound (GHRC) described herein above known to be effective to cause an increase in growth hormone levels in the blood to be administered to the patient for a provocative challenge. The kit also includes an amount of a molecule known to be effective to cause an increase in growth hormone levels in the blood, the molecule being selected from GHRP-6 or an analogue of GHRP-6 which causes release of growth hormone by the same cellular mechanism as GHRP-6 (GHRX). Enough material of each agent is included in order to administer each agent individually for a provocative challenge as well as to co-administer the two agents. The kit can optionally also include the reagents for measuring GH levels in the blood of patients following the provocative challenge. The kit can optionally be configured for testing for multiple patients or for a single patient.

There are a number of factors that are relevant to understanding the underlying basis of the hypothesis which lead to the present invention both in determining the etiology of short stature in children and in understanding the etiology of GH deficiencies in adults and children as discussed herein below. The interpretation of these factors is not to be construed as limiting the present invention to this one mode of action.

Recent studies show that GHRH may not be the only endogenous agent that provides stimulation for GH secretion. A xenobiotic hexapeptide, GHRP-6, which has different binding characteristics from GHRH (Codd et al., 1989; Blake, et al., 1991) and utilizes a different somatotroph second messenger system (Cheng et al., 1989) is a GH secretagogue that potentiates GHRH efficacy (Bowers et al., 1990). Furthermore, like GHRH, GHRP-6 is effective in some, but not all, short-statured children or adults to whom it is administered (Bowers et al., 1991; Merica et al., 1992). The different mechanisms and synergistic effects of GHRH and GHRP-6, in vitro and in vivo, suggested to applicants the existence of an endogenous analogue for the synthetic hexapeptide that may be physiologically relevant. Initial support for this hypothesis derives from one study in which passive immunization against endogenous GHRH in rats, reduced GHRP-6 activity approximately 90% (Bercu et al., 1992a). These data demonstrated the requirement of endogenous GHRH for expression of GHRP-6 activity.

This unexpected reciprocal relationship, i.e., dependence of GHRH upon an endogenous analogue of GHRP-6, is the basis of the present invention. Thus, in individuals deficient in the endogenous GHRP-6 analogue, GHRH efficacy would be blunted, whereas in individuals deficient in GHRH, GHRP-6 efficacy would be blunted. However, Robinson, et al. (1992) taught that GHRP-6 efficacy was not dependent upon endogenous GHRH. It was therefore unexpected for applicants to find the interdependence of the GH secretagogues.

Further support for the present invention derives from applicants' recent finding in which old rats that were hyporesponsive to individually administered GHRH or GHRP-6, were hyperresponsive to co-administered GHRH and GHRP-6 (Walker et al., 1992; Bercu et al., 1992b). Hyposensitivity to the individually administered peptides suggested that more than one, interdependent, endogenous, stimulatory factor contributed to GH secretion.

The progressive decrement of GH or age-related loss of GHRH efficacy, as seen in aging, could result from several factors. One of these factors could be that chronic reduction in pituitary stimulation by GHRH causes desensitization to the GH secretagogue because hormones often induce their own receptors. Support for reduced stimulation of the pituitary by GHRH derives from the fact that available and/or appropriate GH secretagogues seem to decline during aging (De Gennaro Colonna et al., 1989; Morimoto et al., 1988; Ono et al., 1986). However, an alternative hypothesis has been suggested by applicants that age-related, reduced efficacy of GHRH may be due to the absence or reduced concentrations of other, yet undefined, endogenous co-secretagogue(s) (Goth et al., 1992).

Deficits in pituitary GH concentrations observed in animals may also contribute to age-related insensitivity to GHRH and subsequent GH deficiency (Bercu et al, 1992b; Walker et al, 1994a). However, depletion of pituitary GH may not occur in humans because the only published report states that pituitary GH concentrations did not vary significantly with age when measured at autopsy (Gershberg, 1957). However, this report has not been corroborated by other investigators and applicants have shown that in old laboratory animals, pituitary GH concentrations are significantly lower than in young animals of the same species. The low concentrations of pituitary GH in old animals are probably not due to inherent defects in pituitary function, but more likely to reduced stimulation of the gland. Support for this view derives from the fact that pituitary GH concentrations, as well as pituitary GH mRNA, were significantly increased in old rats chronically administered GHRH and GHRP-6 (Walker et al., 1994a).

As discussed herein above, it has been hypothesized that a factor having the potential to reduce GHRH efficacy during aging is deterioration of GHRH-pituitary-binding-sites. GHRH binding sites with high and low affinities have been identified on rat pituitary membranes (Abribat et al., 1990). Since decreased capacity and loss of the high affinity site correlated with reduced GH secretion during aging, it was suggested that the high affinity binding site mediates GHRH action in somatotrophs (Abribat et al., 1991). Prior to this GHRH binding study, applicants (Codd et al., 1989) reported that GHRP-6 has two binding sites on pituitary and hypothalamic membranes. GHRH did not compete for these GHRP-6 binding sites, suggesting that the two peptides bind different entities. These differential binding sites may be functionally related, since somatotrophs lacking GHRH receptors are unresponsive to GHRP administered alone (Jansson et al., 1986), or in combination with GHRH (Bercu et al., 1992a).

Functional linkage has been demonstrated many times in the ability of GHRP-6 to enhance GHRH efficacy (Cheng et al., 1989; Bowers et al., 1990), and applicants showed that passive immunization against GHRH reduced GHRP activity approximately 90% (Bercu et al., 1992a). The ability of GHRP-6 to increase GHRH activity in aging rats (Walker et al., 1991) may result from facilitation of GHRH binding through cooperativity/allosteric interactions. Changes in intracellular transduction of GHRH has also been associated with aging. GHRH-activated adenylate cyclase activity and cAMP concentrations were lower in pituitaries from old rats than from young ones (Ceda et al., 1986; Parenti et al., 1987; Parenti et al., 1991). However, this apparent deficit was immediately reversed by co-administration of GHRH and GHRP-6 in vivo (Walker et al., 1991), again suggesting cooperativity between the peptides and deficiency or loss of a co-secretagogue(s) for GHRH during aging. Similarly, gene defects involving transcription of GH mRNA could account for reduced synthesis and secretion of GH in the elderly, and applicants showed that GHRH and GHRP-6 administered together positively affect the molecular biology of GH endocrinology in old rodents (Walker et al., 1994b).

Finally, age-related loss of GHRH efficacy could result from increased exposure of the pituitary gland to somatostatin (SRIF; Shibasaki et al., 1984; Sonntag and Gough, 1988; Sonntag et al., 1980), a peptide that inhibits GH secretion. Passive immunization with SRIF antiserum increased GH release more in old rats than in young rats (Sonntag et al., 1981; Sonntag and Gough, 1988), and reduced pulsatile GH secretion in aging female rats (Sonntag et al., 1980); correlated with SRIF hypersecretion (Takahashi et al., 1987). In a clinical study, administration of the acetylcholinesterase inhibitor pyridostigmine to block endogenous SRIF release partially restored GH responsiveness to GHRH in elderly subjects (Ghigo et al., 1990). Direct measurement of hormones released from perfused hypothalamic explants confirmed increased SRIF secretion from tissues of old rats (Ge et al., 1989).

It has been proposed that the activity of GHRP-6 is greater in vivo than in in vitro because the hexapeptide is a functional antagonist of SRIF, perhaps acting at the pituitary to prevent SRIF hyperpolarization of the somatotroph (DeBell et al., 1991; Goth et al, 1992; Jaffe et al., 1992). These possibilities are consistent with applicants finding that co-administration of the complementary GH secretagogues, GHRH and GHRP-6 immediately restore youthful patterns of GH secretion in old animals (Walker et al., 1991, Walker et al., 1994 a,b).

Figure 1A:
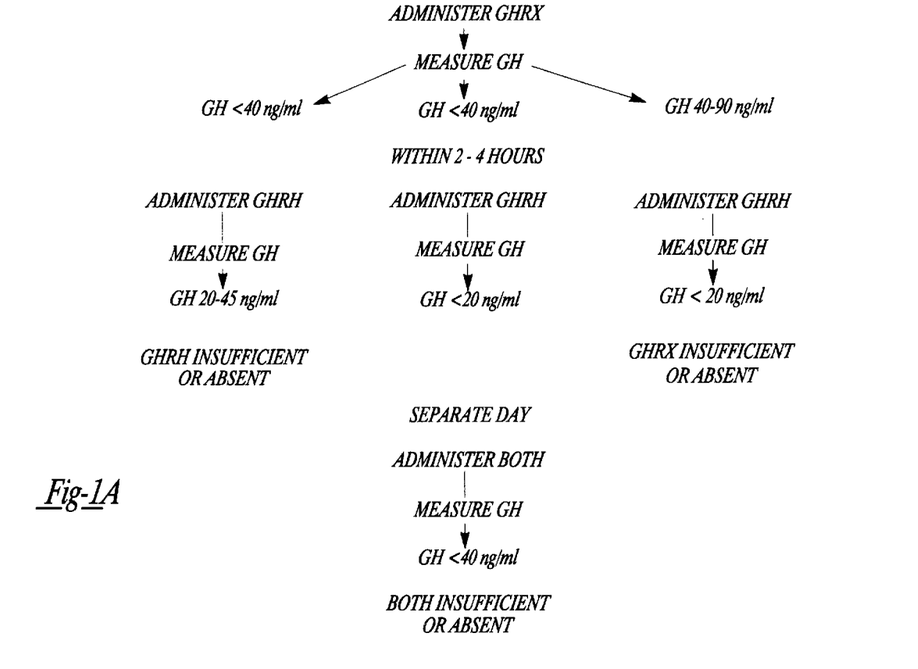
FIGS. 1A–1B are diagrams of the three step provocative testing protocol of the present invention.
Figure 1B:
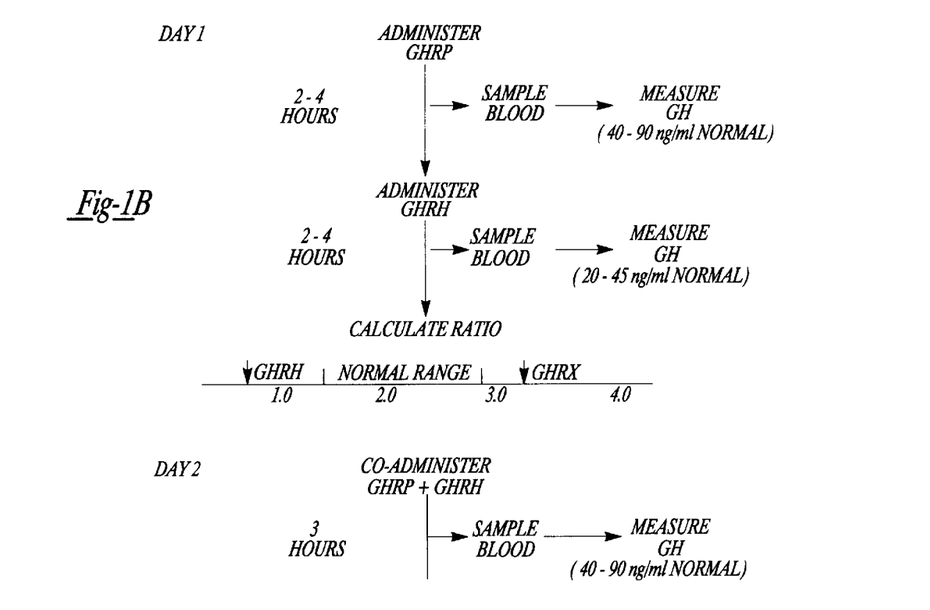

Therefore, age-related pituitary GH hyposecretion probably reflects decrements in the combined influence of several peptides, including SRIF on the pituitary, requiring analysis of responses to co-administered substances as provocative, diagnostic challenges. This hypothesis is in agreement with a report in which GH regulation was shown to be complex, involving several secretagogues acting in concert with GHRH to provide tightly controlled, temporal and quantitative secretion of GH (Goth et al., 1992). Accordingly, applicants devised a model for direct testing of pituitary, growth hormone secretory capability (FIGS. 1A–1B). The model assumes that a "normal" response to administration of exogenous GHRP-6 or GHRH requires the presence of its endogenous analogue, i.e., GHRH or GHRP, respectively. Blunted responses to either exogenous GH secretagogue is interpreted as indicating a deficiency of its endogenous complement. Blunted responses to both exogenous GH secretagogues, administered sequentially, implies deficiencies of both endogenous complements. This condition can be differentiated from inherent pituitary problems such as those involving receptor or second messenger deficits by a "normal" response to GHRH and GHRP co-administration. A blunted response following co-administration of both GH secretagogues would indicate inherent pituitary dysfunction rather than inadequate endogenous stimuli.

Thus, the present invention provides a new clinical application for the co-secretagogues GHRP-6 and GHRH and other synthetic GH secretagogues that function by the same mechanism as GHRP-6 or GHRH. The invention is important because it not only provides a reliable method for identifying children and adults with low GH secretory capability, but also helps diagnose the etiology of GH deficiency and provides a key to appropriate treatment.

Once a child or adult is diagnosed as having either a deficiency in either or both endogenous GHRH and GHRP, the appropriate replacement therapy can ensue whereby either a growth hormone releasing compound, a GHRP-6 or analogue thereof or a combination of both GH secretagogues is administered to the child or adult.

Robinson et al. (1992) has stated that endogenous GHRH does not contribute to the effect of a provocative dose of GHRP. If this were correct, then a poor response to GHRP would suggest a defect in the mechanism for GHRP-6 signal transduction/processing, when in fact it could simply result from deficient complement (endogenous GHRH). As the result of the conclusion of Robinson et al. (1992) that endogenous GHRH does not contribute to endogenous GHRP-6-like activity, the therapy resulting from a poor GHRX provocative test would be GHRP-6 replacement in an attempt to "prime" the pituitary to respond or, failing that, to use recombinant GH therapy. Therefore, by the conclusion of the Robinson et al. (1992) diagnostic procedure and those of his colleagues, especially Bowers, GHRH replacement would not be indicated in a patient who responded poorly to GHRP-6, even though GHRH deficiency could be the possible cause of such poor response to a GHRP-6 provocative challenge.

The above discussion provides a factual basis for the method of differential diagnostic protocol and kit for evaluating pituitary growth hormone (GH) secretory capability as a means to identify the etiology of GH deficiency. The methods used with and the utility of the present invention can be shown by the following examples.

EXAMPLES

Animals

Fischer 344 rats (Charles River), both male and female, were used. Young animals are defined as sexually mature between 2 and 7 months of age. Old animals are defined as those over 16 months of age.

EXAMPLE 1

GHRH-efficacy has been reported to be reduced 50 to 75% in old rats (Sonntag et al., 1983); therefore, applicants tested the effect of GHRP-6 alone and in combination with GHRH on GH release in old rats. Peak plasma GH concentrations resulting from GHRP-6 administration in old rats were approximately 60% less than in young rats. In contrast, peak plasma GH concentrations were greater in old rats than in young rats administered GHRP-6 and GHRH. Since target organs sometimes become hyperresponsive when tonic and/or phasic stimulation decreases, than one would expect exaggerated responses to provocative exogenous stimuli under experimental conditions. GH hypersecretion observed in naive, old rats administered a single bolus of GHRH and GHRP (Walker et al., 1991) provides support for the hypothesis that deficits in stimulated GH secretion in aged rats were due to insufficient signals or inappropriately transduced GH releasing stimuli.

The first possible cause of age-related decrements in GH secretion that applicants considered was that a progressive reduction in pituitary stimulation occurs during aging. This reduction could be attributed to GHRH and/or to an endogenous ligand for GHRP-6. Although the search has begun, a purported endogenous ligand for GHRP-6 has not yet been identified (Bercu et al., 1992a). Nonetheless, applicants were able to demonstrate the functional dependence of GHRP-6 upon endogenous GHRH by causing deficits in GHRH that, in turn, attenuated responses to GHRP-6 (Bercu et al., 1992a).

Young rats were passively immunized against endogenous GHRH or administered α-methyl-p-tyrosine. If GHRH and the endogenous ligand of GHRP-6 are physiological co-agonists of GH secretion in the young rat, then removal of one or the other should be expressed as attenuated activity of its co-agonist when administered alone. Passive immunization which inactivates GHRH with neutralizing antibodies, or α-methyl-p-tyrosine (L form) which blocks stimulation of hypothalamic GHRH neurons were used to remove or reduce concentrations of endogenous GHRH in the young experimental animals. These treatments were intended to simulate the aged condition in which concentrations of GHRH and GHRH mRNA are low (De Gennaro Collona et al., 1989; Morimoto et al., 1988). Afterwards, GHRP-6 was administered to test and compare its efficacy with that in old rats (Walker et al., 1991).

Figure 2:
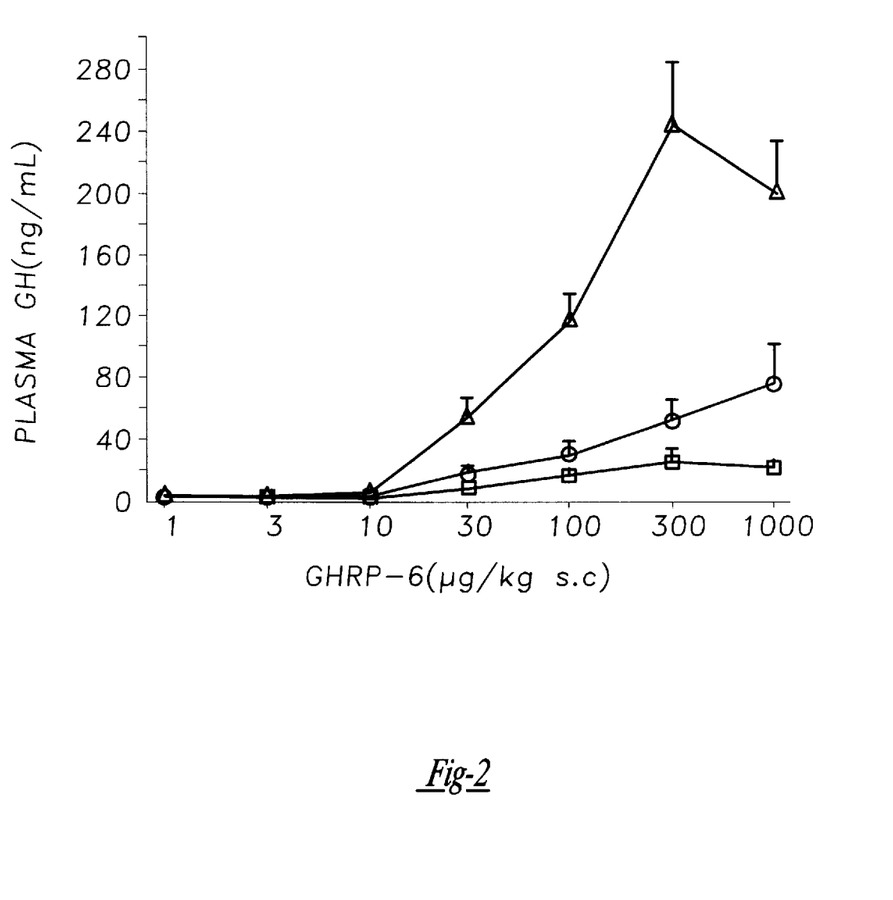
FIG. 2 is a dose response curve for GHRP-6 in rats pretreated with vehicle (triangles), α-methyl-p-tyrosine (circles), or GHRH antiserum (squares). Values represent means±SEM (8 rats per dose and treatment) in plasma collected 15 minutes after administration of GHRP-6.

As seen in FIG. 2, GHRP-6 activity was significantly attenuated in young female rats administered GHRH antiserum or α-methyl-p-tyrosine to reduce endogenous GHRH concentrations. Presumably, naturally occurring decrements in endogenous GHRH during aging contributed to the blunted response to GHRP-6 that applicants observed (Walker et al., 1991). If GHRH activity is also dependent upon a yet unidentified endogenous co-secretagogue whose concentrations decline during aging, then applicants' data support the hypothesis that extrinsic pituitary deficits contribute, at least in part, to attenuated GH secretory responses to administered GHRH.

The second possible cause of age-related decrements in GH secretion applicants considered was that deterioration in GH secretagogue signal transduction at the pituitary level contributes to the progressive insensitivity to provocative stimuli. In a test of this hypothesis, applicants examined GH secretory responses to GHRP-6 in young rats administered [N-Ac-Tyr$^1$, D-Arg$^2$]-GRF 1-29, an antagonist to the pituitary GHRH receptor.

Figure 3A:
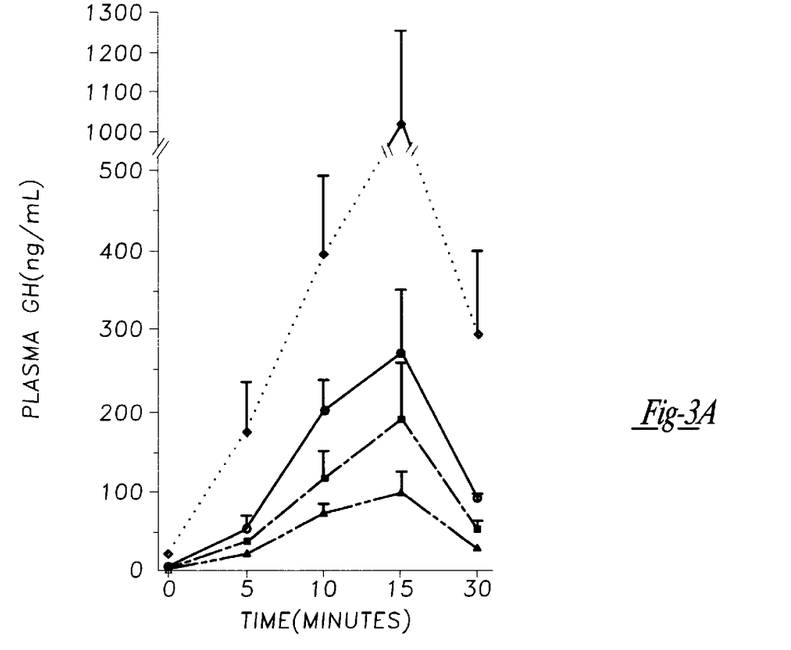
FIGS. 3A–3B are dose response curves showing the effect of [N-Ac-Tyr$^1$, D-Arg$^2$]-GRF 1-29 amide, a GHRH receptor antagonist, on GH release in response to GHRP-6 (30 µg/kg, closed symbols, FIG. 3A) or morphine (1.5 mg/kg, open symbols, FIG. 3B). The GHRH receptor antagonist was administered in doses of 0 (circle), 5 (square), 50 (triangle), or 150 (diamond) µg/kg. Values represent mean±SEM 8 rats per group.
Figure 3B:
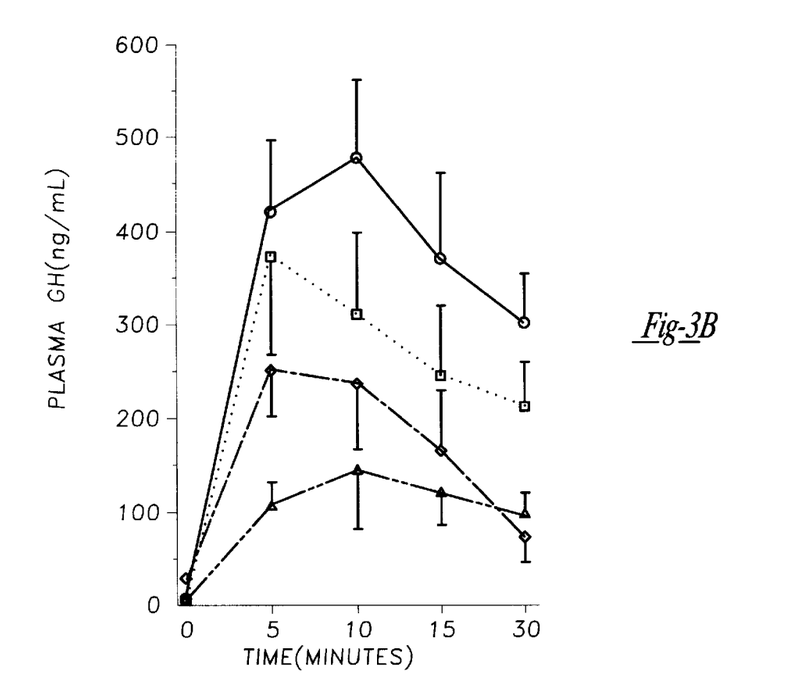

As seen in FIG. 3A–3B, pre-administration of 5 to 50 μg/kg of [N-Ac-Tyr$^1$, D-Arg$^2$]-GRF 1-29 amide which blocks pituitary GHRH receptors also attenuated GHRP activity. However, 150 μg/kg of [N-Ac-Tyr$^1$, D-Arg$^2$]-GRF 1-29 amide potentiated GHRP-6 activity, presumably due to partial agonist activity of the GHRH receptor agonist at the higher dose (Bercu et al., 1992a). GHRP-6 stimulated GH secretion as a function of time was significantly reduced ($P<0.05$) by 50 mg/kg GHRH receptor antagonist and significantly increased ($P<0.01$) by 150 mg/kg GHRH receptor antagonist (FIG. 3A). Morphine-stimulated GH secretion was significantly reduced ($P<0.05$) by 50 and 150 mg/kg GHRH receptor antagonist (FIG. 3B).

These data suggest that activation of pituitary GHRH receptors contributes to full expression GHRP activity in vivo.

EXAMPLE 2

A study in children has been performed. The results of this study support the basic concept of GH secretagogue complementarity as a useful diagnostic tool for evaluating pituitary-based, GH deficiency.

The protocol used in the pediatric study from which data presented below were collected involved the sequential administration of exogenous GHRP and exogenous GHRH as set forth in the present invention (Table 4; FIGS. 1A–1B). Briefly, each subject began testing at approximately 0900 h, one half hour after placement of an intravenous catheter. Two blood samples for basal concentrations of serum GH were drawn, and GHRP (1 μg/kg) was administered as a bolus. Blood samples were then drawn at five minute intervals for 20 minutes during which the GH secretory response occurred, and at longer intervals for about two hours thereafter.

GHRH (1 μg/kg) was then administered as a bolus, when basal GH concentrations were again established. Blood samples were similarly collected after GHRH administration as they were following GHRP administration. GH concentrations in each serum was then determined by radioimmunoassay.

The study population was composed of children with normal GH secretory function (serving as controls and normal baseline values) and those with GH secretory dysfunction of various clinical diagnoses. The purpose of evaluating different etiologies of GH secretory dysfunction was to validate the hypothesis that complementary endogenous GH secretagogues must be present for optimal expression of GHRP or GHRH stimulatory potential.

Figure 4A:
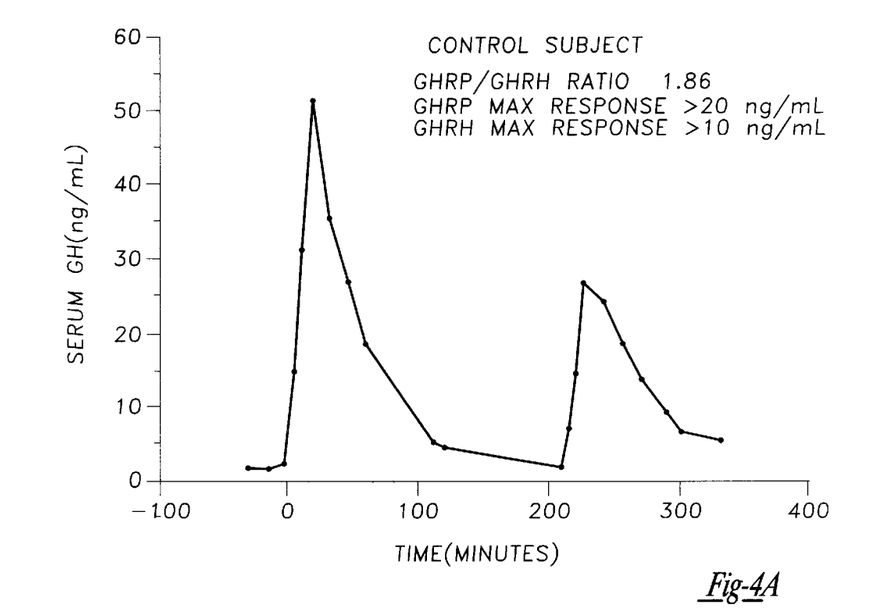
FIGS. 4A–4D are a series of dose response curves showing GH concentration over time and the calculated ratio of maximal GH responses after GHRP-6 vs. GHRH challenge in (4A) a control subject, (4B) a hypopituitary subject, (4C) a constitutional delay subject, and (4D) an irradiated subject.

As seen in FIG. 4A, peak concentrations of serum GH were reached at the 15 or 20 minute time point following stimulation with both secretagogues. In all five normal children tested, peak GH concentrations following GHRP-6 administration were greater than those following GHRH administration.

Peak concentrations of serum GH following GHRP-6 administration in normal children ranged between 42 and 66 ng/ml, whereas peak concentrations of serum GH following GHRH administration ranged between 18 and 36 ng/ml. Thus, the ratio of GHRP-6 to GHRH evoked responses in the normal children ranged between 1.8 (66/36) and 2.3 (42/18), reflecting the greater responses to GHRP-6 in these subjects.

Three primary assumptions about these data were used with the data collected from children with GH secretory dysfunction. These assumptions were that:

1. peak concentrations of serum GH following administration of exogenous GHRP-6 or GHRH reflected not only the dose of GH secretagogue administered, but also the "normal concentration" of endogenous complementary GH secretagogue present in the subject;
2. GHRP-6:GHRH ratios between 1.4 and 2.5 (allowing for standard errors) reflected the "normal concentrations" of endogenous GH secretagogues contributing to the peak concentrations measured in normal individuals; and
3. peak concentrations of serum GH in response to exogenous GHRP-6 or GHRH should occur within 15 or 20 minutes of their administration.

With these considerations in mind, applicants tested children with various causes of GH secretory dysfunction ranging from hypopituitarism to that resulting from radiation therapy. The results of these tests substantiated the basic premises of the test hypothesis.

Figure 4B:
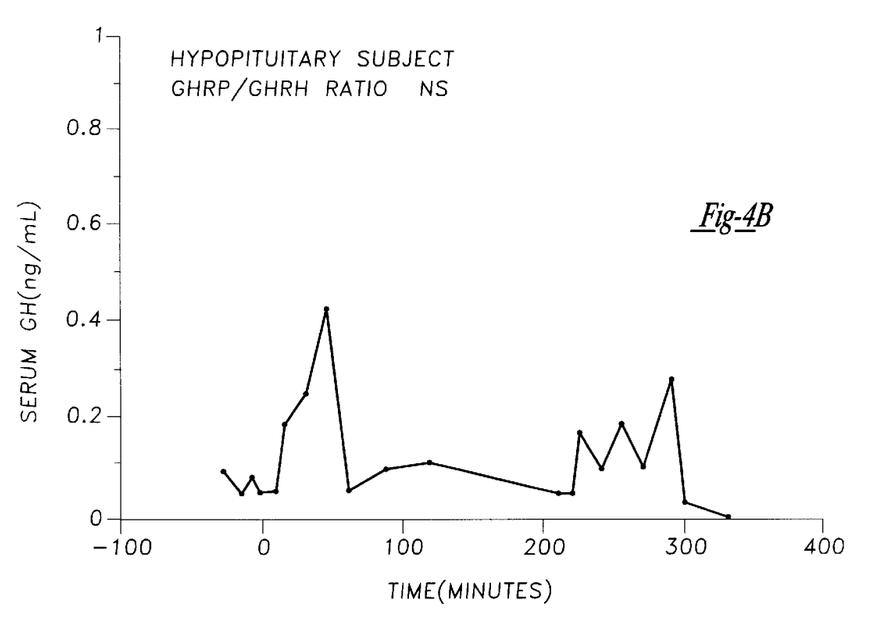

The data presented in FIG. 4B show that children with inherently dysfunctional pituitary glands did not respond to any combination of exogenous GH secretagogue administration. This representative subject had atrophic, developmentally retarded pituitary gland which responded to neither sequentially administered GHRP and GHRH nor to the co-administered peptides.

Radiation of the head for treatment of cancer in children retards growth, presumably by reducing the secretion of endogenous GHRH from hypothalamic neurosecretory neurons. In this clinical study, children that were presumably deficient in endogenous GHRH responded poorly to GHRP-6, but exuberantly to GHRH, resulting in a GHRP:GHRH ratio significantly <1. As seen in FIG. 4D, a representative subject from this group produced a peak response of 18.9 ng/ml serum GH in response to GHRP-6, whereas the response to GHRH was 49.4 ng/ml, resulting in a GHRP to GHRH ratio of 0.38. The data were interpreted to mean that the poor response to GHRP-6 resulted from a paucity of endogenous GHRH after radiation. The reduced availability of this GHRP complement, therefore, attenuated the response to a provocative dose of exogenous GHRP-6. Conversely, the data also suggest that radiation did not alter the availability of the endogenous analogue GHRP because the response to a provocative dose of GHRH was amplified. This finding could be explained by enhanced sensitivity of the pituitary to GHRH resulting either from increased exposure to the endogenous analogue of GHRP and/or by a mechanism involving low level exposure to GHRH that, in turn, increased the pituitary response to a substantial bolus of the secretagogue. The actual mechanism of this change in responsivity is unknown, but data collected from other patients suggest that the reciprocal affect also occurs.

Figure 4C:
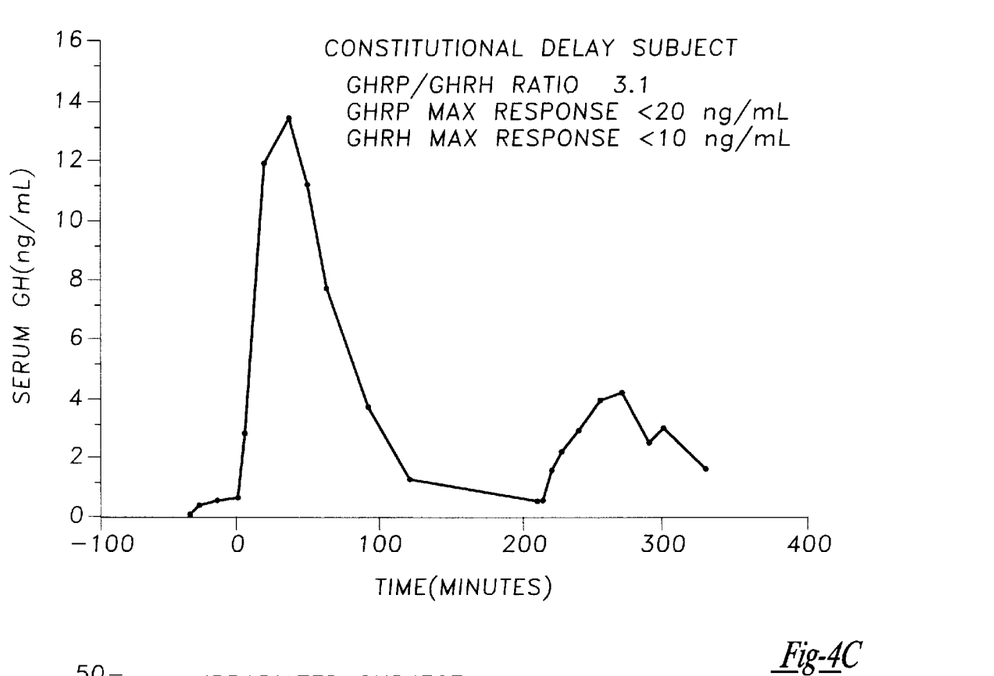
Figure 4D:
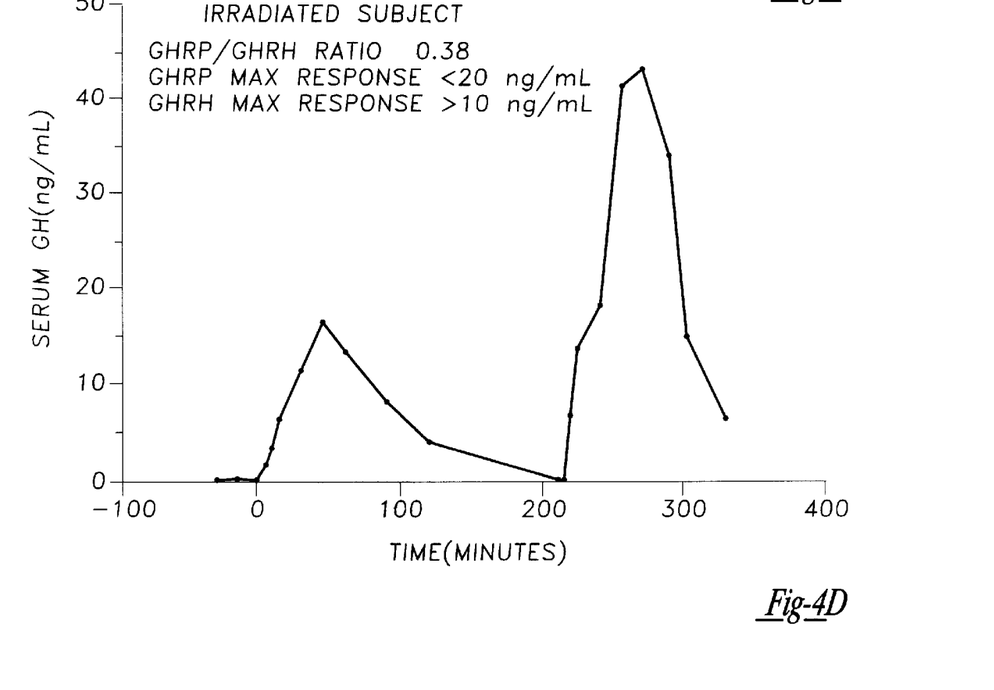

As seen in FIG. 4C, some children responded poorly to both secretagogues, but much better to GHRP than to GHRH. This pattern of response suggests a greater deficiency in endogenous GHRP than in GHRH giving a GHRP:GHRH ratio >3. A peak response of 13.5 ng/ml serum GH occurred after administration of GHRP-6, whereas a peak response of only 4.4 ng/ml occurred after administration of GHRH. The GHRP to GHRH ratio for this subject was 3.1.

Interestingly, in all individuals with GHRP to GHRH ratios greater than 3, the quantitative responses to both exogenous secretagogues were significantly lower than those observed in normal subjects. These data suggest that the endogenous analogue of GHRP-6 deficiency may be more tightly linked to GHRH deficiency than the reciprocal, because as shown above, quantitatively normal and even supranormal responses to GHRH can occur in the presence of poor responses to exogenous GHRP-6. This observation suggests that endogenous GHRH deficiency is not necessarily accompanied by endogenous GHRP deficiency. However, since applicants have not observed quantitatively normal responses to exogenous GHRP-6 in the presence of poor responses to GHRH, a deficit in endogenous GHRP may always be accompanied by a deficit in GHRH.

An interesting and logical extension of these observations is to differentiate the responses of individuals with GHRP to GHRH ratios of <1 from those with ratios >3, because in GH deficient animals which provide a more homogenous population than humans, co-administration of GHRH and GHRP produced supranormal GH secretory responses (Walker et al., 1991). In limited studies with GH deficient human subjects, Bowers et al. (personal communication) observed attenuated mean (population) responses to the co-administered GH secretagogues. However, he did not screen the subjects for their individual responses to GHRP and GHRH, so that the variance in his data could result from differences in the endogenous secretagogues, i.e. robust responders may have had GHRP to GHRH ratios >3, while poor responders had ratios <1.

Throughout this application various publications are referenced. Full citations for the referenced publications not included herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Albini et al., "Diagnostic value of the growth hormone-releasing factor stimulation test", *Clinical Pharmacol Ther.*, 43:696–700 (1988)

Abribat et al., "Characterization of [$^{125}$I-Tyr$^{10}$] human growth hormone-releasing factor (1–44) amide binding to rat pituitary: evidence for high and low affinity classes of sites", *Brain Res.* 528-291–299 (1990)

Abribat et al., "Alterations of pituitary growth hormone-releasing factor binding sites in aging rats", *Endocrinology* 128:633–635 (1991)

Bercu et al., "Role of selected endogenous peptides in growth hormone releasing hexapeptide (GHRP-6) activity", *Endocrinology*, 130:2579–2586 (1992a)

Bercu et al., "Structural and Functional Responses of Aged Female Rats to Chronic Co-Administration of Growth Hormone Releasing Hormone (GHRH) and GH Releasing Hexapeptide (GHRP-6)", *Endocrinol.* (Abstract) Annual Meeting San Antonio, Tex., Jun. 24–27, 1992, pg. 182 (1992b)

Blake and Smith, "Desensitization studies using perifused rat pituitary cells show growth hormone-releasing hormone and His-D-Trp-Ala-Trp-D-Phe-Lyns-NH$^2$ stimulate growth hormone release through distinct receptor sites", *J. Endocrinol.*, 129:11–19 (1991)

Bowers et al., "Structure-Activity Relationships of Synthetic Pentapeptide that Specifically Releases Growth Hormone in Vitro", *Endocrinol.* 106:663–667 (1980)

Bowers et al., "Growth Hormone (GH)-Releasing Peptide Stimulates GH Release in Normal Men and Acts Synergistically with GH Releasing Hormone, *J. Clin. Endocrinol. Metab.* 70:975–982 (1990)

Bowers et al., "Growth Hormone-releasing activity of a synthetic hexapeptide in normal men and short statured children after oral administration", *J. Clin. Endocrinol. Metab.* 74:292–298 (1991)

Butenandt, "Diagnostic value of growth hormone-releasing hormone in short children" *Acta Paediatr. Scand* [suppl.] 349:93–99) (1989)

Ceda et al., "Diminished pituitary responsiveness to growth hormone-releasing factor in aging male rats", *Endocrin.* 118:21090–2114 (1986)

Chatelain et al., "Growth Hormone (GH) Response to Single Intravenous Injection of Synthetic GH-Releasing Hormone in Prepubertal Children with Growth Failure", *J. Clin. Endocrinol. Metab.* 65:387–394 (1987)

Cheng et al., "Synergistic effects of HIS-D-TRP-ALA-TRP-D-PHE-LYS-NH$_2$," *Endocrinol.* 124:2791–2798 (1989)

Codd et al., "Binding of growth hormone releasing hexapeptide to specific hypothalamic and pituitary binding sites", *Neuropharmacology* 28:1139–1144 (1989)

DeBell et al., "Growth hormone (GH) secretion during continuous infusion of GH-releasing peptide: Partial response attenuation", *J. Clin. Endocrinol. Metab.* 72:1312–1316 (1991)

DeGennaro Colonna et al., "Reduced growth hormone releasing factor (GHRF)-like immunoreactivity and GHRF gene expression in hypothalamus of aged rats", *Peptides* 10:705–708 (1989)

Devesa et al., "Reasons for the variability in growth hormone (GH) responses to GHRH challenges: the endogenous hypothalamic-somatotroph rhythm (HSR)", *Clinical Endocrinology* 30:367–377 (1989)

Finkelstein et al., "Age-related change in 24-hour spontaneous secretion of growth hormone", *J. Clin. Endocrinol. Metab.* 35:665–670 (1972)

Ge et al., "Relationship between growth hormone-releasing hormone and somatostatin in rat: effects of age and sex on content and in vitro release from hypothalamic explants", *J. Endocrinol* 123:53–58 (1989)

Ghigo et al., "Pyridostigmine partially restores GH responsiveness to GHRH in normal aging", *Acta endocrinol.* 123:169–174 (1990)

Goth et al., "Pituitary adenylate cyclase activating polypeptide, growth hormone (GH)-releasing peptide and GH-releasing hormone stimulate GH release through distinct pituitary receptors", *Endocrinology* 130:939–944 (1992)

Ho et al., "Effects of sex and age on 24-hour profile of growth hormone secretion in man: Importance of endogenous estradiol concentrations", *J. Clin. Endocrinol. Metab.* 64:51–57 (1987)

Howard et al., "A Receptor in Pituitary and Hypothalamus That Functions in Growth Hormone Release", *Science* 273:874–877 (1996).

Iovino et al., "Repetitive growth hormone-releasing hormone administration restores the attenuated growth hormone (GH) response to GH-releasing hormone testing in normal aging", *J. Clin. Endocrinol. Metab* 69:910–913 (1989)

Jansson et al., "The dwarf little (Lit/Lit) mouse is resistant to growth hormone releasing peptide (GHRP-6) as well as to GH releasing hormone (GHRH)", *Endocrine Society Abstracts, Annual Meeting* (1986)

Kaiser et al., "Effect of recombinant human growth hormone on malnourished older individuals", *J. Am. Geriatr. Soc.* 39:235–240 (1991)

Lang et al., "Effects of sex and age on growth hormone response to growth hormone-releasing hormone in healthy individuals", *J. Clin. Endocrinol. Metab.* 65:535–540 (1987)

Lang et al., "The influence of age on human pancreatic growth hormone releasing hormone stimulated growth hormone secretion", *Horm. Metabol. Res.* 20-574–578 (1988)

Marcus et al., "Effects of short term administration of recombinant human growth hormone to elderly people", *J. Clin. Endocrino. Metab.* 70:519–527 (1990)

Morimoto et al., "Age-related changes in growth hormone releasing factor and somatostatin in rat hypothalamus", *Neuroendocrinology* 47:459–464 (1988)

Martha et al., "A persistent pattern of varying pituitary responsivity to exogenous growth hormone (GH)-releasing hormone in GH-deficient children: evidence supporting periodic somatostatin secretion", *J. Clin. Endocrinol. Metab.* 67:449–454 (1988)

Merica et al.: Growth Hormone Responses to a Second Generation Growth Hormone Releasing Peptide and to GH Releasing Hormone [GHRH] in Growth Hormone Deficient Children, *Endocrine Society Abstracts*, 74th Annual Meeting, San Antonio, Tex., June 24–27, No. 477, pg 171 (1992)

Momany et al., "Design, Synthesis, and Biological Activity of Peptides which Release Growth Hormone in Vitro", *Endocrinol.* 108:31–39 (1981)

Momany et al., "Conformational Energy Studies and in Vitro and in Vivo Activity Data on Growth Hormone-Releasing Peptides", *Endocrinol.* 114:1531–1535 (1984)

Ono et al., "Release of immunoreactive growth hormone-releasing factor (GRF) and somatostatin from incubated hypothalamus in young and old male rats", *Neuroendocrinology* 43:111 (abstract) (1986)

Parenti et al., "Different regulation of growth hormone-releasing factor-sensitive adenylate cyclase in anterior pituitary of young and aged rats", *Endocrinology* 121:1649–1653 (1987)

Pavlov et al., "Responses of growth hormone (GH) and somatomedin-C to GH-releasing hormone in healthy aging men", *J. Clin. Endocrinol. Metab.* 62:595–600 (1986)

Pertzelan et al., "Plasma growth hormone response to synthetic GH-RH1-44 in 52 children and adults with growth hormone deficiency of various etiologies", *Hormone Res* 22:24–31 (1985)

Robinson et al., "Acute growth hormone (GH) response to GH-releasing hexapeptide in humans is independent of endogenous GH-releasing hormone",*J. Clin. Endocrinol. Metab.* 75:1121–1124 (1992)

Root and Oski, "Effects of human growth hormone in elderly males", *J. Gerontol* 24:97–104 (1969)

Rudman et al., "Impaired growth hormone secretion in adult population" *J. Clin. Invest.* 67:1361–1369 (1981)

Rudman et al., "Effects of human growth hormone in men over 60 years old", *New Eng. J. Med.* 323:1–6 (1990)

Schriock et al., "Effect of growth hormone (GH)-releasing hormone (GRH) on plasma Gh in relation to magnitude and duration of GH deficiency in 26 children and adults with isolated GH deficiency or multiple pituitary hormone deficiencies: Evidence for hypothalamic GHR deficiency", *J. Clin. Endocrinol. Metab.* 58:1043–1049 (1984)

Shibasaki et al., "Age-related changes in plasma growth hormone response to growth hormone-releasing factor in man", *J. Clin. Endocrinol. Metab.* 58:212–214 (1984)

Smith et al., "Nonpeptidyl Growth Hormone Secretagogue", *Science* 260:1640–1643 (1993)

Sonntag et al., "Decreased pulsatile release of growth hormone in old male rats", *Endocrinology* 107:1875–1879 (1980)

Sonntag et al., "Effects of CNS active drugs and somatostatin antiserum on growth hormone release in young and old male rats", *Neuroendocrinology* 33:73–78 (1981)

Sonntag et al., "Impaired ability of old male rats to secrete growth hormone in vivo but not in vitro in response to hpGRF (1-44)", *Endocrinology* 113:2305–2307 (1983)

Sonntag et al., "Growth hormone releasing hormone induced release of growth hormone in aging male rats: dependence on pharmacological manipulation of endogenous somatostatin release", *Neuroendocrinology* 47:482–488 (1988)

Takahashi et al., "Growth hormone secretory patterns in young, middle-aged and old female rats. *Neuroendocrinolgy* 46:137–142 (1987)

Tannenbaum et al., "Paradoxical enhancement of pituitary growth hormone (GH) responsiveness to GH-releasing factor in the face of high somatostatin tone" *Endocrinology* 124:1380–1388 (1989)

Walker et al., "Robust growth hormone (GH) secretion in aged female rats co-administered GH-releasing hexapeptide (GHRP-6) or GH releasing hormone (GHRH)", *Life Science* 49:1499–1504 (1992)

Walker et al., "Effects of stimulated growth hormone secretion on age-related changes in plasma cholesterol and hepatic low density lipoprotein messenger RNA concentrations", *Mechanisms of Aging and Development* 75:215–226 (1994a)

Walker et al., "Effects of growth hormone secretagogues on age-related changes in the rat immune system", *Endocrine* 2:857–862 (1994b)

Wehrenberg and Ling, "Absence of age-related change in pituitary response to growth hormone-releasing factor in rats", *Neuroendocrinology* 37:463–466 (1983)

What is claimed is:

1. A method for determining pituitary growth hormone (GH) secretory capability after secretagogue challenge, as an indication of GH secretory deficiency in a patient comprising the steps of a) establishing a baseline level of growth hormone in a blood sample of the patient;

b) administering to the patient a first secretagogue molecule (GHRX), selected from the group (GHRX) consisting of GHRP-6, wherein GHRP-6 is a hexapeptide of amino acid sequence His-D-Trp-Ala-Trp-D-Phe-Lys-$NH_2$, and an analogue which causes release of GH from the pituitary gland by a cellular mechanism that is the same as for GHRP-6, in an amount known to be effective for causing an increase in blood GH levels of normal patients;

measuring levels of GH in blood samples taken from the patient during a time of 120 minutes after said GHRX administration;

within two to four hours after said GHRX administration, administering to the patient a second secretagogue molecule (GHRH), selected from the group consisting of growth hormone releasing hormone and analogues thereof, in an amount known to be effective for causing an increase in blood GH levels of normal patients;

measuring levels of GH in blood samples taken from the patient during a time of 120 minutes after said GHRH administration;

c) on a day different from that on which said step b) is performed, co-administering to the patient a combination of GHRH and GHRX, each in an amount known to be effective to cause an increase in blood GH levels of normal patients; and measuring levels of GH in blood samples taken from the patient after said co-administration;

d) comparing the levels of GH measured after said GHRX administration, after said GHRH administration, and after said co-administration with one another and with levels of GH similarly measured in normal patients thereby indicating GH secretory deficiency in the patient.

2. The method of claim 1 wherein the response to the GHRX and GHRH secretagogues is evaluated by calculating a ratio of peak GH levels following GHRX administration divided by peak GH levels following GHRH administration.

3. The method of claim 1 wherein the growth hormone releasing hormone analogues are selected from the group consisting of GH releasing factor and any of peptidyl or non-peptidyl synthetic analogues that release GH from the pituitary gland by a same cellular and molecular mechanism as growth hormone releasing hormone.

4. The method of claim 1 wherein the analogue which causes release of growth hormone by the same cellular mechanism as GHRP-6 is selected from the group consisting of GHRP-1;

Tyr-D-Trp-Gly-Phe-Met-$NH_2$;

Tyr-D-Phe-Gly-Phe-Met-$NH_2$;

Trp-D-Phe-Pro-Phe-Met-COOH;

Tyr-Ala-D-Trp-Phe-Met-$NH_2$;

Tyr-D-Trp-D-Trp-Phe-Met-$NH_2$;

Tyr-D-Trp-D-Trp-Phe-$NH_2$;

Tyr-D-Trp-D-Trp-Phe-COOH;

D-Trp-D-Trp-Phe-$NH_2$;

His-D-Trp-Ala-Trp-D-Phe-$NH_2$;

Tyr-D-Trp-Ala-Trp-D-Phe-$NH_2$;

His-D-Trp-D-Trp-Ala-Trp-D-Phe-Lys-COOH

His-D-Trp-Ala-Trp-D-Phe-Arg-$NH_2$; and

L-692,429, ((3(R)-amino-3-methyl-N-(2,3,4,5-tetrahydro-2-oxo-1)-(2'-(1H-tetrazole-5-yl)-(1,1'-biphenyl)4-yl)(methyl-1H-1-benzazepin-3yl) butanamide mono(hydrochloride)dihydrate.

5. The method of claim 1 wherein the amount of GHRH administered is 100 ng/kg to 1 mg/kg of body weight.

6. The method of claim 1 wherein the amount of GHRX administered is 100 ng/kg to 1 mg/kg of body weight.

7. The method of claim 1 wherein the amount being co-administered of GHRH is 100 ng/kg to 1 mg/kg of body weight and the amount of GHRX is from 100 ng/kg to 1 mg/kg of body weight.

8. The method as set forth in claim 1 wherein the patient is a child with short stature.

* * * * *